United States Patent [19]
Wiedner

[11] Patent Number: 5,357,292
[45] Date of Patent: Oct. 18, 1994

[54] EYEGLASSES WITH ADJUSTABLE TEMPLE INCLINATION

[75] Inventor: Klaus Wiedner, Fürth, Fed. Rep. of Germany

[73] Assignee: Uvex Safety, LLC, Smithfield, R.I.

[21] Appl. No.: 64,504

[22] Filed: May 18, 1993

[30] Foreign Application Priority Data

May 26, 1992 [DE] Fed. Rep. of Germany ... 9207109[U]

[51] Int. Cl.$^5$ ............................ G02C 5/20; A61F 9/02
[52] U.S. Cl. ..................... 351/105; 351/106; 351/107; 351/109; 351/115; 351/121; 2/450; 2/453
[58] Field of Search ........................... 2/450, 451, 453; 351/41, 44, 47, 57, 59, 103, 104, 105, 106, 107, 109, 115, 121

[56] References Cited

U.S. PATENT DOCUMENTS

| | | | |
|---|---|---|---|
| 2,563,125 | 8/1951 | Malcom, Jr. | 2/450 |
| 3,233,249 | 2/1966 | Baratelli et al. | 351/44 |
| 3,233,250 | 2/1966 | Jonassen | 351/44 |
| 3,901,589 | 8/1975 | Bienenfeld | 351/47 |
| 4,527,291 | 7/1985 | Nussbickl | 2/450 |
| 4,843,655 | 7/1989 | Hegendörfer | 2/449 |

Primary Examiner—William L. Sikes
Assistant Examiner—David R. Parsons
Attorney, Agent, or Firm—Salter & Michaelson

[57] ABSTRACT

In glasses, in particular industrial safety or sports glasses with an integral continuous sight piece and with inclination-adjustable side pieces articulated on a frame piece it is provided for the purpose of defined and reliable inclination-adjustment accompanied by the advantage of low-cost manufacturing that the sight piece has lateral backwards oriented appendixes formed in one piece with it and extending about in parallel to the wearer's head, that a frame piece with lateral appendixes is arranged along the upper edge of the sight piece surrounding the latter and the latter's appendixes, that the frame piece with the articulated side pieces is supported on the sight piece pivotably around a horizontal pivot axis, in that pins are arranged on the inside of each of the appendixes, that the pins engage with semicircular slits concentric of the pivot axis in the appendixes of the sight piece, wherein, to arrest the pins in certain angular positions of the slits, the latter are formed by a plurality of approximately annular locking recesses intersecting to form locking protrusions and approximately corresponding to the cross-section of the pin.

4 Claims, 2 Drawing Sheets

EYEGLASSES WITH ADJUSTABLE TEMPLE INCLINATION

BACKGROUND OF THE INVENTION

1. Field of the Invention

The invention relates to a pair of glasses, in particular industrial safety or sports glasses, with an integral continuous sight piece and with inclination-adjustable side pieces articulated on a frame piece.

2. Background Art

Glasses of the generic type have, on the one hand, a particularly simple structure realizable by pure plastics technology, on the other hand a sight piece of this configuration will ensure excellent adaptation to the wearer's anatomy and reliable protection of the eyes against light and occurring particles.

To increase the wearing comfort and for optimum adaptation to the wearer's anatomy it is also known to arrange the side pieces inclination-adjustably on the sight piece.

In a successful prior solution it is for instance provided that locking protrusions are arranged inside on lateral appendixes of the frame and engage with recesses in the side portion of the sight piece.

However, this construction implies a problem in terms of manufacturing technique, i.e. for the rationalization of manufacturing the locking recesses must be produced when the sight piece is injection-molded and will consequently be covered again when a coating is subsequently applied to the sight piece to increase scratch resistance or to realize anti-misting properties, so that in the ultimate condition for use, i.e. after the coating has cured, they are no longer deep enough to ensure a reliable and defined locking effect.

SUMMARY OF THE INVENTION

It is accordingly the object of the invention to structure a pair of glasses of the generic type such that in any case reliable adjustment and maintenance of the sidepiece inclination referred to the sight piece is ensured at a little expense of manufacturing technique and independently of a surface coming to be applied to the sight piece.

In accordance with the invention this object is attained in that the sight piece has lateral backwards oriented appendixes formed in one piece with it and extending about in parallel to the wearer's head, in that a frame piece with lateral appendixes is arranged along the upper edge of the sight piece surrounding the latter and the latter's appendixes, in that the frame piece with the articulated side pieces is supported on the sight piece pivotably around a horizontal axis, in that pins are arranged on the inside of each of the appendixes of the frame piece, in that the pins engage with semicircular slits concentric of the pivot axis in the appendixes of the sight piece, wherein, to arrest the pins in certain angular positions of the slits, the latter are formed by a plurality of approximately annular locking recesses intersecting to form locking protrusions and approximately corresponding to the cross-section of the pin.

As a result of this solution the semicircular slits serve on the one hand as guiding slits and simultaneously in combination with the pins as an interlocking arrangement for the setting of a certain angle of inclination. The slits of this type are indifferent to a coating being applied, i.e. an operative and reliable adjusting and arresting effect is achieved in any case and in particular even after a prolonged use.

Advantageously it is provided that retaining heads, which can be entered into the slits and when entered will overlap the latter, are provided on the inside of the pips. It is thus ensured that the frame piece does not disengage from the sight piece in its normal condition of use.

The horizontal pivot axis is most simply defined by a pivot bearing formed by a central pin on the inside of the frame piece and a recess in the middle of the sight piece, the pin engaging with this recess with little play.

To achieve a certain elastic flexibility in the change of the locking positions, a further slit can be provided to extend in parallel to each slit that constitutes the locking bearings. In particular, it is feasible to provide a slit extending in parallel on both sides of each slit that constitutes the locking bearings. In this way webs are formed which define the locking bearing slit elastically flexibly. In particular, provision can be made for the contour of the inner edge of each outer slit to follow the contour of the locking beating slits.

In the following the invention is more closely described on the basis of a preferred example of embodiment taken in conjunction with the drawing.

DESCRIPTION OF THE PREFERRED EMBODIMENT

Figure 1:
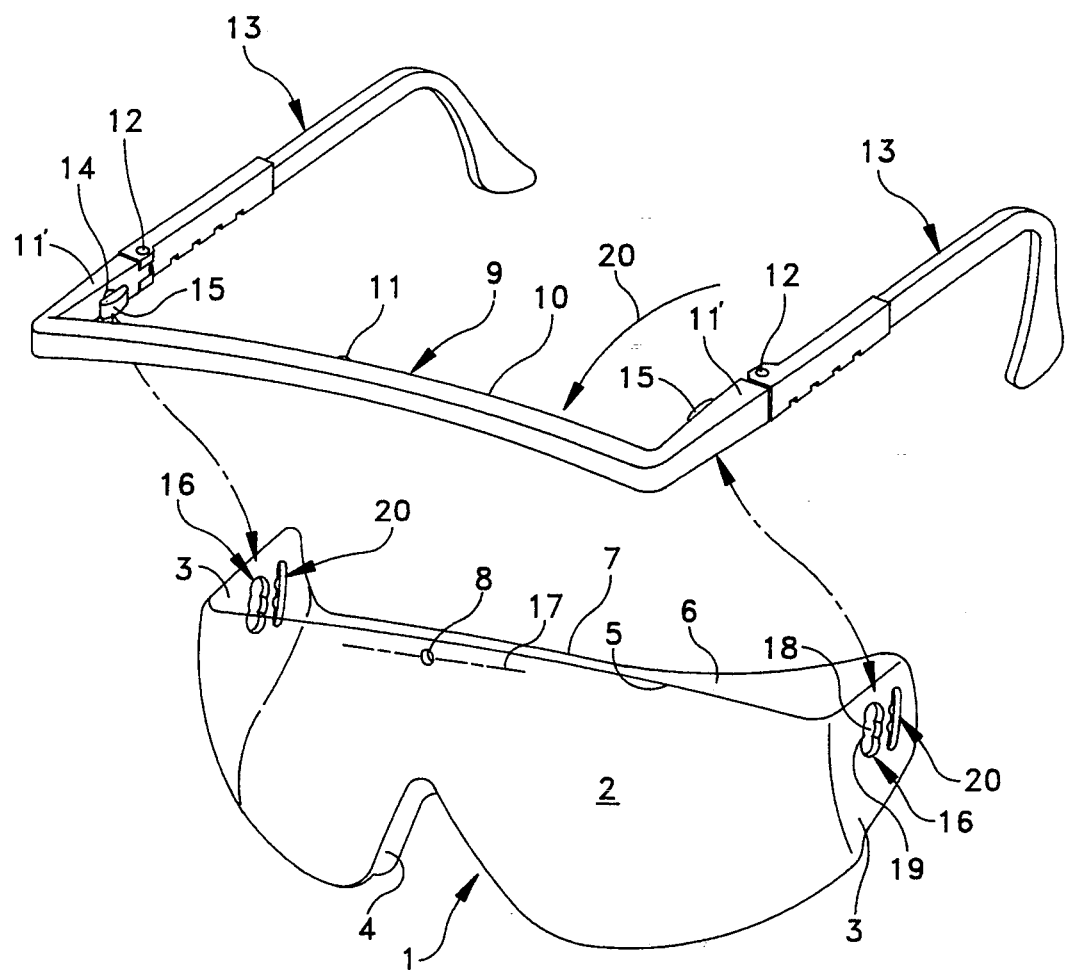
FIG. 1 is a perspective view of a pair of glasses according to the invention, the frame piece being not yet mounted to the sight piece.

A pair of glasses illustrated in the drawing comprises a sight piece 1 injection-molded in one piece from plastic material and having a continuous front sight field 2 followed by lateral appendixes 3 turning off backwards approximately at right angles. A nose piece 4 expanding the bearing face is integrally formed in the vicinity of the wearer's nose bridge. An appendix 6, which is horizontal in the wearing condition, extends from the upper edge 5 of the sight piece backwards with a rear edge 7 arched corresponding to the forehead anatomy.

A bearing recess 8 in the form of a circular bore is formed in the middle of the sight field 2 underneath the upper edge 5.

A frame piece 9 comprises a section 10 extending in parallel to the upper edge 5 of the sight field 2 in the assembled condition, a bearing pin 11 engaging with the bearing recess 8. The frame section 10 is followed by frame appendixes 11' turning off backwards by about 90° with a hinge 12 of conventional structure for side pieces 13, which are length-adjustable in the example of embodiment.

Pins 14 with a retaining head 15 are formed on the inside of the frame appendixes 11'.

The lateral frame appendixes 11' extend in parallel to the lateral appendixes 3 of the sight piece 1 and surround the latter.

Slits 16 are formed in the lateral appendixes 3 of the sight piece 1 and extend concentrically of the pivot bearing axis 17, which is defined by the recess 8 and the pin 11.

The slits 16 are formed by a plurality of intersecting circular recesses 18 separated from each other by locking protrusions 19. The diameter of the recesses 18 corresponds about to the diameter of the pins 14, so that by reason of the locking protrusions 19 the pins 14 can be pivoted from one such recess 18 into the next while overcoming the locking force, a certain angle of inclination of the side pieces, i.e. a defined angle of inclination, being preset by each of these recesses 18.

For the assembly of the frame piece 9 on the sight piece 1 the frame piece is pivoted by 90° referred to the position of use shown in the drawing, so that the retaining heads 15 may pass through the slits 16.

If the frame piece 9 is then pivoted in the direction of the arrow 20, the pin 11 can lockingly engage with the recess 8 and the retaining heads 15 overlap the slits 16 so that a amble status is reached which nevertheless ensures the side pieces 13 inclusive of the frame piece 10 to be pivoted in relation to the sight piece 1.

Figure 2:
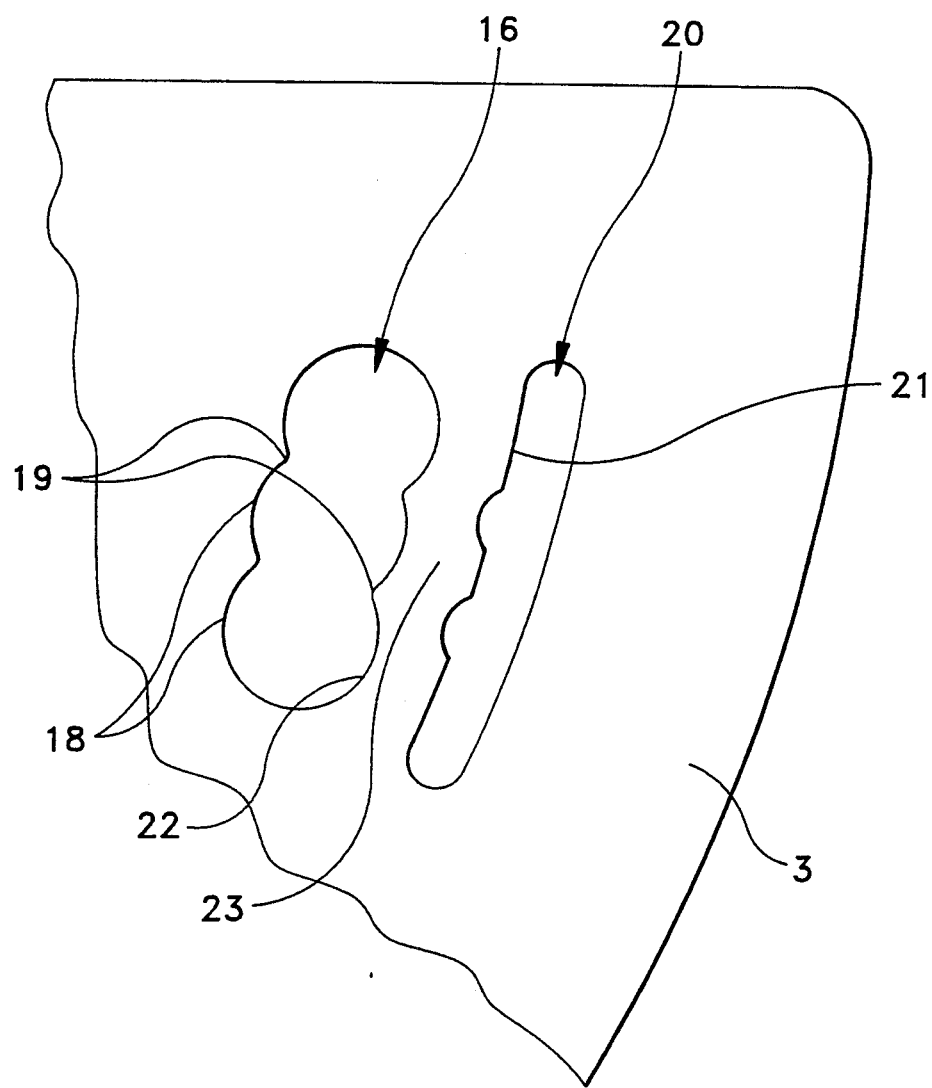
FIG. 2 is a detailed view of the slit area.

As seen in particular in FIG. 2, another slit 20 extends at a certain distance in parallel to each slit 16 and its inner edge 21 follows in contour about the contour of the edge 22 of the locking slit 16, so that a web 23 forms between the slits 16 and 20, which can give way elastically when the position of inclination is adjusted, i.e. upon transition from one locking position to the next. The resistance against adjustability, or in other words the locking force, can be defined and set by the dimensioning of the web 23 and of the slit 20, respectively, which as such might also still be provided on the other side of the locking slit 16.

What is claimed is:

1. Glasses, in particular industrial safety or sports glasses, with an integral continuous sight piece and with inclination-adjustable side pieces articulated on a frame piece, wherein the sight piece (1) has lateral backwards oriented appendixes (3) formed in one piece with it and extending about in parallel to the wear's head, wherein a frame piece (9) with lateral appendixes (11') is arranged along the upper edge (5) of the sight piece (1) surrounding the latter and the latter's appendixes (3), wherein the frame piece (9) with the articulated side pieces (13) is supported on the sight piece (1) pivotably around a horizontal pivot axis (17), wherein pins (14) are arranged on the inside of each of the appendixes (11'), wherein the pins (14) engage with semicircular slits (16) concentric of the pivot axis (17) in the appendixes (3) of the sight piece (1), wherein, to arrest the pins (14) in certain angular positions of the slits (16), the latter are formed by a plurality of approximately annular locking recesses (18) intersecting to form locking protrusions (19) and approximately corresponding to the cross-section of the pin (14), and wherein at least one further slit (20) extends at a distance in parallel to the slit (16) with the locking protrusions (19) to form an elastic web (23) located in between.

2. Glasses according to claim 1, wherein a retaining head (15), which overlaps the slit (16), is arranged at the free end of each pin (14).

3. Glasses according to claim 1, wherein in the middle of the sight piece (1) underneath its upper edge (5) an approximately circular recess (8) is arranged, with which a pin (11) on the inside of the frame piece (9) engages forming a pivot bearing with the pivot axis (17).

4. Glasses according to claim 1, wherein the contour of the inner edge (21) of the slit (20) extends parallel to the adjacent edge (22) of the slit (16).

* * * * *